United States Patent [19]
Aster et al.

[11] Patent Number: 5,972,717
[45] Date of Patent: Oct. 26, 1999

[54] METHOD AND KIT FOR DETECTING HEPARIN INDUCED THROMBOCYTOPENIA

[75] Inventors: Richard H. Aster, Milwaukee; Gian Visentin, Shorewood, both of Wis.

[73] Assignee: The Blood Center Research Foundation, Inc., Milwaukee, Wis.

[21] Appl. No.: 08/974,331

[22] Filed: Nov. 19, 1997

Related U.S. Application Data

[63] Continuation of application No. 08/438,470, May 10, 1995, abandoned.

[51] Int. Cl.$^6$ .............................. C12Q 1/56; C12Q 1/28; G01N 33/53; G01N 33/563
[52] U.S. Cl. .......................... 436/503; 427/2.13; 435/7.1; 435/7.2; 435/7.9; 435/7.92; 435/7.94; 435/13; 435/28; 435/961; 435/970; 435/975; 436/501; 436/503; 436/513; 436/518; 436/529; 436/174; 436/175; 436/176; 436/530; 436/531; 436/532; 436/808
[58] Field of Search ............................ 427/2.13; 435/7.1, 435/7.2, 7.94, 13, 28, 961, 970, 975, 7.9, 7.92; 436/501, 503, 513, 518, 529, 174, 175, 176, 530, 531, 532, 808, 811, 825; 514/54

[56] References Cited

U.S. PATENT DOCUMENTS

| | | | |
|---|---|---|---|
| 4,613,665 | 9/1986 | Larm | 536/20 |
| 4,707,471 | 11/1987 | Larm et al. | 514/54 |
| 4,717,654 | 1/1988 | Savoca et al. | 435/7.9 |
| 4,795,745 | 1/1989 | Larm et al. | 514/54 |
| 4,810,784 | 3/1989 | Larm | 536/20 |
| 5,049,403 | 9/1991 | Larm et al. | 427/213 |
| 5,213,898 | 5/1993 | Larm et al. | 428/422 |
| 5,446,582 | 8/1995 | Amiral | 435/7.9 |
| 5,466,582 | 11/1995 | Amiral | 435/7.9 |

FOREIGN PATENT DOCUMENTS

| | | | |
|---|---|---|---|
| WO 92/02823 | 2/1992 | France | 435/13 |

OTHER PUBLICATIONS

J.G. Kelton et al., "Immunoglobulin G From Patients with Heparin–Induced Thrombocytopenia Binds to a Complex of Heparin and Platelet Factor 4," *Blood*, 83(11): 3232–3239 (Jun. 1, 1994).

R. H. Aster, "The Immunologic Thrombocytopenias," *Platelet Immunobiology Molecular and Clinical Asepcts* J.B. Lippincott Company, Philadelphia, PA, pp. 387 and 392, 1989.

J. Amiral, et al., "Antibodies to Macromolecular Platelet Factor 4–Heparin Complexes in Heparin–induced Thrombocytopenia: a Study of 44 Cases," *Thrombosis and Haemostatis* 73:21–28, 1995.

D. J. Christie, et al., "Drug–Antibody–Platelet Interaction in Quinine– and Quinidine–induced Thrombocytopenia," *J. Clin. Invest.* 70:989–998, 1982.

D. J. Christie, et al., "Fab–mediated Binding of Drug–dependent Antibodies to Platelets in Quinidine– and Quinine–induced Thrombocytopenia," *J. Clin. Invest.* 75:310–314, 1985.

(List continued on next page.)

*Primary Examiner*—James C. Housel
*Assistant Examiner*—Gailene R. Gabel
*Attorney, Agent, or Firm*—Quarles & Brady LLP

[57] ABSTRACT

A method of detecting heparin-induced antibodies to complete a diagnosis of heparin-induced thrombocytopenia (HITP) is disclosed. This method comprises the first step of attaching a glycosaminoglycan to a solid support, wherein the glycosaminoglycan is attached to the solid support only at the reducing end of the molecule (unidirectionally). Platelet factor 4 is then bound to the glycosaminoglycan forming a complex having an epitope recognizable by antibodies generated in an HITP immune response. Human blood plasma or serum from a patient suspected of having HITP is exposed to the complex and the complex is analyzed to determine if HITP-related antibodies are present. A device and kit used in performing the diagnostic assay are also disclosed.

25 Claims, 7 Drawing Sheets

OTHER PUBLICATIONS

M. N. Fukuda, et al., "Survival of Recombinant Erythropoietin in the Circulation: The Role of Carbohydrates," *Blood* 73(1):84–89, 1989.

M. Galli, et al., "Anti–Glycoprotein Ib/IX and IIb/IIIa Antibodies in Patients with Antiphospholipid Antibodies," *Thrombosis and Haemostasis* 71(5):571–575, 1994.

J. Hoffman, et al., "A new method for covalent coupling of heparin and other glycosaminoglycans to substances containing primary amino groups," *Carbohydrate Research* 117:328–331, 1983.

L. LaFrance, et al., "Improved Heparin–Agarose: Higher Loading and Greater Stability," in *Sigma Com.*, pp. 2 and 3, 1995 (advertising communication from Sigma Chemical Co.).

O. Larm, et al., "Surface–immobilized heparin," in Heparin: Chemical and Biological Properties; Chemical Applications, D.A. Lane, U. Lindahl Eds., CRC Press, Boca Raton, Florida pp. 597–608, 1989.

O. Larm, et al., "Coupling of proteins and other amines to carboydrate polymers via bromine oxidation and reductive amination," *Carbohydrate Research* 58:249–251, 1977.

R. J. Linhardt, et al., "Isolation and Characterization of Human Heparin," *Biochemistry* 31:12441–12445, 1992.

F. J. Morgan, et al., "Complete Covalent Structure of Human Platelet Factor 4," *Thrombos. Haemostas.* 42:1652–1660, 1979.

V. D. Nadkarni, et al., "Directional Immobilization of Heparin onto Beaded Supports," *Analytical Biochemistry* 222:59–67, 1994.

Sigma Com, "Improved Heparin–Agarose: Higher Loading and Greater Stability" pp. 2–3. * same.

G. P. Visentin, et al., "Determinants on Heparin:PF4 Complexes Recognized by Antibodies Associated with Heparin–Induced Thrombocytopenia/Thrombosis (HITP)," *Blood* 4[10]:Suppl. 1, 1994. Abstract No. 968.

G. P. Visentin, et al., "Characteristics of Quinine– and Quinidine–Induced Antibodies Specific for Platelet Glycoproteins IIb and IIIa," *Blood* 77(12):2668–2676, 1991.

G. P. Visentin, et al., "Antibodies Associated with Heparin–Induced Thrombocytopenia and Thrombosis (HITP) Recognize Platelet Factor 4 (FR) Bound to Heparin or Endothelial Cell Glycosaminoglycans (GAG)," *Blood* 82(Suppl. 1):163a, 1993 (abstract No. 634).

G. P. Visentin, et al., "Antibodies from Patients with Heparin–induced Thrombocytopenia/Thrombosis are Specific for Platelet Factor 4 Complexed with Heparin or Bound to Endothelial Cells," *J. Clin. Invest.* 93:81–88, 1994.

G. P. Visentin, et al., "A Prospective Study of the Formation of Antibodies Reactive with Heparin:PF4 Complexes in Patients Treated with Heparin," Abstract, 1994, ASH Meeting, Dec. 2–4, 1994.

X. Zhang, et al., "Crystal Structure of Recombinant Human Platelet Factor 4," *Biochemistry* 33:8361–8366, 1994.

Ihrcke et al., "Role of Heparan Sulfate in Immune System—Blood Vessel Interactions," *Immunology Today* 14:500–505, 1993.

Amiral, J. et al., "Antibodies to Macromolecular Platelet Factor 4–Heparin Complexes in Heparin–induced Thrombocytopenia: a Study of 44 Cases," Thrombosis and Haemostasis, 73:21–28, Jan. 1995.

Nadkarni, V.D. et al., "Directional Immobilization of Heparin onto Beaded Supports," Analytical Biochemistry, 222:59–67, 1991.

Pierce Derivatized Polystyrene Beads, Advertisement, 1995.

Sigma Chemical Company Advertisement, L. LeFrance et al., "Improved Heparin–Agarose: Higher Loading and Greater Stability," Sigma.com, pp. 2–3, 1995.

Visentin, G. et al., "Antibodies from Patients with Heparin–induced Thrombocytopenia/Thrombosis Are Specific for Platelet Factor 4 Complexed with Heparin or Bound to Epithelial Cells," Journal of Clinical Investigation, 93:81–88, Jan. 1994.

(2) β-D-glucuronic acid
(a) R = H   (b) R = $SO_3^-$ (4) N-acetyl-α-D-glucosamine
(a) R = H   (b) R = $SO_3^-$ (1) α-L-iduronic acid
(a) R = H   (b) R = $SO_3^-$ (3) N-sulfo-α-D-glucosamine
(a) R = R' = H   (b) R = $SO_3^-$   R' = H
(c) R = R' = $SO_3^-$   (d) R = H   R' = $SO_3^-$

```
HPF4  E S S F P A T F V P   V T R A S P L P A D S     E A E E D G D L Q C L C V K T
RPF4                                                  E A E E D S D L Q C V C V K T
BPF4                                                  E G G E D L Q C V C L K T 20                        30                    40
HPF4  T S Q V R P R H I T S L E V I K A G P H C P T A Q L I A T
RPF4  S S S R I H L K R H I T S L E V I K A G P H C A V P L I A T
BPF4  T S G I N P R H I S S L E V I G A G T H C P S P Q L L A T 50                    60                        70
HPF4  L K N G R K I C L D D L Q A P L Y K K I I K K L L E S
RPF4  L K N G S K I C L D D R Q V P L Y K K I I K K L L E S
BPF4  K K T G R K I C L D Q Q R P L Y K K L L K K L L D G D E S

Single underline =    RPF4 aminoacids not homologous to HPF4 aminoacids.
Double underline =    RPF4 aminoacids not homologous to HPF4 aminoacids, to be
                      mutated for "rat scanning mutagenesis".

Bold             =    putative heparin binding domain.
```

FIG. 5

METHOD AND KIT FOR DETECTING HEPARIN INDUCED THROMBOCYTOPENIA

This is a continuation, of application Ser. No. 08/438,470 filed May 10, 1995 now abandoned.

FIELD OF THE INVENTION

In general, the present invention relates to heparin-induced thrombocytopenia/thrombosis (HITP) and its detection. Specifically, the invention includes a method for diagnostic uses relating to anchored heparin/PF4 (platelet factor 4) complexes which are recognized by a heparin-induced antibody.

BACKGROUND

Thrombocytopenia (low blood platelet levels) is most often caused either by defective platelet production or excessive platelet destruction. Defective platelet production is a common manifestation of many toxic, nutritional, and neoplastic disturbances of the bone marrow. Increased peripheral destruction of platelets is characterized by shortened platelet survival and increased proliferation of bone marrow megakaryocytes in an effort to compensate for the low platelet levels. Frequently, this process is immunologically mediated.

Certain drugs and their metabolites induce antibodies in some individuals which can cause immune platelet destruction. Implicated drugs include quinidine and quinine (stereoisomers of each other), sulfonamide antibiotics and many others (R. H. Aster, in *Platelet Immunobiology: Molecular and Clinical Aspects.* T. J. Kunicki and J. N. George eds., Lippincott, Philadelphia, pp. 387–435, 1989; N. R. Shulman, et al., "Platelet Immunology" in *Hemostasis and Thrombosis: Basic Principles and Clinical Practice.* R. W. Culman, J. Hirsh, V. J. Marder, E. W. Salzman, eds. Lippincott, Philadelphia, 2nd ed., pp. 452–529, 1989). A few of these drugs, such as penicillin, appear to bind covalently to platelet proteins and stimulate the formation of antibodies specific for the drug-protein complex (hapten-dependent antibodies) (D. J. Salamon, et al., *Transfusion* 24: 395, 1984). More often, however, the sensitizing drug or one of its metabolites induces the formation of antibody by an unknown mechanism (Aster, supra, 1989; A. Salama, et al., *Sem. Hematol.* 29: 54–63, 1992). The resulting antibodies bind to platelets only in the presence of drug to cause platelet destruction. Evidence obtained by the Applicants (D. J. Christie, et al., *J. Clin. Invest.* 75: 310, 1985; D. J. Christie, et al., *J. Clin. Invest.* 70: 989, 1982) and others (C. Mueller-Eckhardt, et al., *Trans. Med. Rev.* 4: 69, 1990; A. Salama, et al., *Semin. Hematol.* 29: 54, 1992) indicates that in such cases, the drug binds non-covalently and reversibly to selected platelet membrane proteins to induce conformational changes or form compound epitopes that are recognized by the antibodies. Drug-dependent binding of the antibodies to platelets causes the platelets to be destroyed. In the several forms of drug-induced immune thrombocytopenia, platelet counts are often very low and bleeding complications are frequently severe.

A third type of drug-induced thrombocytopenia (heparin-induced thrombocytopenia or HITP) occurs in patients treated with heparin to prevent or treat thrombosis. Heparin is a family of polysaccharide species consisting of chains made up of alternating, 1-4 linked and variously sulfated residues of glucuronic acid or iduronic acid and D-glucosamine. (B. Casu, "Methods of structural analysis" in Heparin: *Chemical and Biological Properties, Clinical Applications*, D. A. Lane and U. Lindahl, eds. CRC Press, Inc. Boca Raton, Fla., 1989, pp. 25–49.) In man and animal species, heparin is normally found in storage granules of mast cells (tissue basophils) (L. Enerback, "The mast cell system." In *Heparin: Chemical and biological properties, clinical applications*, D. A. Lane and U. Lindahl eds. CRC press, Inc., Boca Raton, Fla., pp. 97–114, 1989). Heparin-like molecules, such as heparan sulfate and chondroitin sulfate are expressed on the surface of endothelial cells that coat the luminal surface of blood vessels and in other tissues where they are coupled to a protein backbone (syndecan) to form a class of molecules known as proteoglycans (Ihrcke, et al., *Immunology Today* 14: 500–505, 1993). The heparin-like residues on endothelial cell proteoglycans are thought to provide one means by which abnormal clotting is prevented, allowing the circulating blood to remain in a fluid state (J. A. Marcum, et al., "The biochemistry, cell biology, and pathophysiology of anticoagulantly active heparin-like molecules of the vessel wall" in Heparin: *Clinical and Biological Properties, Clinical Applications.* D. A. Lane and U. Lindahl eds., CRC Press, Inc., Boca Raton, Fla., pp. 275–294, 1989). Heparin acts as an anticoagulant by binding to a co-factor protein, anti-thrombin III, in such a way as to enable this protein to inhibit certain activated clotting factors, especially activated Factor X (Xa) and thrombin (IIa) (I. Bjork, et al., "Molecular mechanisms of the accelerating effect of heparin on the reactions between antithrombin and clotting proteases" in *Heparin: Chemical and Biological Properties, Clinical Applications*, D. A. Lane and U. Lindahl eds., CRC Press, Inc., Boca Raton, Fla., pp. 229–255, 1989). Heparin of bovine origin appears to be more likely to cause HITP than heparin of porcine origin (W. R. Bell, et al., *N. Engl. J. Med.* 33: 902, 1980).

Thrombocytopenia in patients with HITP is usually not severe enough to result in bleeding. However, patients with this condition often experience thrombosis in major arteries and/or veins which can be fatal or cause the loss of a limb or a stroke. After discontinuation of heparin in patients with HITP, the platelet levels generally return to normal.

HITP appears to be caused by IgG or IgM antibodies that develop after five or more days of heparin therapy (G. P. Visentin, et al., J. Clin. Invest. 93: 81–88, 1994). These antibodies differ from those associated with other forms of drug-induced thrombocytopenia in that, in the presence of optimal concentrations of heparin, they activate blood platelets, causing the platelets to release the contents of their storage granules and to undergo membrane changes that create sites for the binding of a coagulation factor, fibrinogen, normally present in plasma (B. H. Chong, et al., *Br. J. Haematol.* 64: 347, 1986). The Applicants have shown that antibodies associated with HITP are specific for complexes of heparin and platelet factor 4 (PF4), a basic heparin-binding protein normally present in platelet storage granules (Visentin, et al., 1994, supra).

On the basis of findings made in their laboratory, the Applicants recently proposed the following new hypothesis to explain the development of thrombocytopenia and thrombosis in patients sensitive to heparin (Adapted from G. P. Visentin, et al. J. Clin. Invest. 93: 81–88, 1994): In a patient with IgG antibodies specific for heparin/PF4 complexes who is treated with heparin, a) minimal activation of circulating platelets by heparin alone (C. Eika, *Scand. J. Hematol.* 9: 480, 1972) or by immune complexes consisting of heparin, PF4, and IgG, leads to release of PF4 from platelet alpha-granules in a complex with chondroitin sulfate (S. Huang, et al., *J. Biol. Chem.* 257: 11546, 1982); b) circulating heparin displaces the chondroitin sulfate to form heparin/PF4 complexes (R. Handin, et al., *J. Biol. Chem.* 251: 4273, 198-); c) antibodies bind to heparin/PF4 to form immune complexes in close proximity to the platelet surface; d) these complexes bind to platelet Fc receptors, activate platelets, and release more PF4; e) the additional PF4 released reacts with heparin and IgG to form new immune complexes, promoting further platelet activation and causing thrombocytopenia; and f) PF4 released from platelets in excess of the amount that can be neutralized by available heparin binds to heparan sulfate on endothelial cells to create targets for IgG, IgA, or IgM antibodies leading to antibody-mediated endothelial injury and a predilection to thrombosis or disseminated intravascular coagulation. IgM antibodies, because of their greater capacity for complement activation, may be more destructive to endothelial cells than those of the IgG or IgA classes.

Because of the morbidity and mortality associated with HITP, it is important that the diagnosis be made quickly and accurately in a patient who develops thrombocytopenia while receiving heparin. Failure to make a diagnosis in such patients can lead to continuation of heparin therapy and fatal outcome. Assays used to diagnose other forms of drug-induced thrombocytopenia, i.e., binding of IgG or IgM antibodies to normal target platelets in the presence of drug (R. H. Aster, *The Immunologic Thrombocytopenias in Platelet Immunology*. T. J. Kunicki and J. N. George eds., Lippincott, Philadelphia, Pa., pp. 387–435, 1989) are not useful in detecting antibodies associated with HITP (G. P. Visentin, 1994, supra; H. C. Godal, "Heparin-induced thrombocytopenia" in *Heparin: Chemical and Biological Properties, Clinical Applications*, D. A. Lane and U. Lindahl eds., CRC Press, Inc., Boca Raton, Fla., pp. 533–548, 1989).

Accordingly, diagnostic techniques have been developed that make use of the ability of HITP-associated antibodies to activate platelets in the presence of optimum concentrations of heparin. One such test is the platelet aggregation test which is done by mixing the following reagents together in a test tube: normal platelet-rich plasma coagulated with citrate, heparin at a concentration of about one unit per ml, and plasma or serum from the patient suspected of having HITP. The mixture is incubated at 37° C. and stirred. In a positive reaction, the antibody activates the platelets, causing the platelets to aggregate. The extent of aggregation is measured by an increase in light transmission through the mixture (J. G. Kelton, et al., *Blood* 72: 925–930, 1988). The assay is then repeated using a much higher concentration of heparin, e.g., 100 units per ml. Aggregation with the lower dose of heparin and lack of aggregation with the higher dose constitutes a positive test for HITP antibody.

A second and more sensitive test, also dependent on the ability of HITP antibodies to activate platelets, is the $^{14}$C-serotonin release test (D. Sheridan, et al., *Blood* 67: 27–30, 1986). In this assay, washed, normal donor platelets radiolabeled with $^{14}$C-serotonin are suspended in buffer and test serum. Heparin at a concentration of about 0.1 units per ml is then added and the mixture is agitated for about 30 minutes. In a positive test, $^{14}$C-serotonin is released from the platelets by virtue of their being activated by the HITP antibody (Sheridan, 1986, supra). As with the aggregation test, specificity of the reaction is confirmed by showing that $^{14}$C-serotonin release is inhibited by a high dose of heparin, e.g., 100 units per ml.

Another disclosed method is an assay for heparin-induced IgG antibodies based on their reaction with immobilized complexes of heparin and platelet factor 4 (PF4) (see Amiral, et al., *Thromb. Haemostasis* 68: 95–96, 1992). PF4 is a protein component of platelet alpha granules which is positively charged at neutral pH and is known to be capable of binding to and inhibiting the function of heparin. PF4 for use in the assay can be obtained by cleavage or lysis of normal platelets (see PCT Application W096/02833, 1992). PF4 belongs to a super-family of cytokines called "intercrines" or "chemokines" involved in the mediation of certain immune reactions and other activities (see Masushima, et al., *Cytokines* 1: 2–13, 1989). PF4 has high affinity for heparin (see Handin, et al., *J. Biol. Chem.* 251: 4273–4282, 1976) and is able to neutralize the anticoagulant properties of heparin (see Lane, et al., *Biochem. J.* 218: 725–732, 1984, Machalski, et al., Br. *J. Haematol.* 38: 561, 1978).

The heparin/PF4 assay described by Amiral (supra) is more convenient than the platelet aggregation test and the serotonin release test, which depend on activation of fresh platelets. However, discrepancies were observed when comparing results obtained with the heparin/PF4 assay with those obtained in a platelet aggregation test (see Greinacher, et al., *Transfusion* 34: 381–385, 1994). Thus, a method of diagnosing HITP that combines ease of use with high sensitivity and specificity as compared with the favored serotonin release test is not available.

SUMMARY OF THE INVENTION

The present invention provides a method for detecting heparin-induced antibodies to complete a diagnosis of HITP. The method begins by attaching glycosaminoglycan (GAG) molecules covalently and unidirectionally to a solid support. After attachment of the GAG molecules, platelet factor 4 is added and allowed to bind to the GAG to form a complex having an epitope recognizable by antibodies generated in an HITP immune response. Blood plasma or serum from a patient suspected of having HITP is exposed to the complex, and the complex is then analyzed to determine whether HITP-related antibodies have become associated with it. Preferably, the blood plasma or serum is from a human patient.

In one preferable embodiment of the method, analyzing the complex consists of measuring the quantity of a detectable label. The method further consists of contacting the complex attached to the solid support with an immunological component that binds to human antibody. The immunological component is attached to the detectable label.

In a preferred embodiment, the detectable label is alkaline phosphatase and the quantity of label is measured by adding a substrate to react with the label. Preferably, the substrate used is p-nitrophenyl phosphate (PNPP).

The glycosaminoglycan is preferably selected from the group consisting of heparin, heparin salts, metallic heparinates, heparamine, heparan sulphate, substances containing heparin, and heparin analogs and derivatives. In a most preferred embodiment, the glycosaminoglycan is bovine or porcine heparin. In another embodiment, the glycosaminoglycan is a heparin fragment having 10 or more, preferably between 10 and 20, saccharide residues.

The platelet factor 4 (PF4) is preferably selected from the group consisting of native PF4, recombinant PF4, and PF4 created through chemical protein synthesis techniques. We refer to PF4 created via chemical protein synthesis techniques as "synthetic" PF4.

Preferably, the PF4 is human PF4. PF4 or synthetic peptides containing amino acids found in native PF4 which form epitopes recognized by HITP antibodies when complexed with heparin or other GAG are also suitable for the present invention. In a preferred embodiment, PF4 is obtained by pooling platelets from normal whole human blood and releasing PF4 by adding thrombin-receptor activating peptide (TRAP) T. K. Vu, et al., *Nature* 353: 674–677, 1991.

A kit for diagnosing HITP is provided. This kit comprises a solid support prepared by first attaching a glycosaminoglycan covalently and unidirectionally to the solid support and then linking PF4 to the glycosaminoglycan to form a complex having an epitope recognizable by antibodies generated in an HITP immune response. The kit typically includes a receptacle containing a chemical label for detecting an amount of antibody present as well as a receptacle containing a substrate to the chemical label which reacts with the chemical label to produce a measurable color. Instructions for use are typically included.

Preferably, the chemical label in the kit comprises a component selected from the group consisting of an anti-human IgG/enzyme complex, an anti-human IgM/enzyme complex or an anti-human IgA/enzyme complex or a polyvalent probe that recognizes all three. Preferably, a stabilizing agent is added to the solid support to preserve the ability of the complex to bind with antibody over a period of time and to lower non-specific binding of immunoglobulins to the solid support, thus reducing background.

Other objects, features and advantages of the present invention will become apparent from the following detailed description and examples. The specific examples, while indicating preferred embodiments of the invention, are given by way of illustration only, since various changes and modifications within the spirit and scope of the invention will become apparent to those skilled in the art.

DESCRIPTION OF THE DRAWINGS

FIG. 1A shows a method in which heparin and platelet factor 4 are combined before being adhered to the solid support. FIG. 1B shows a method in which PF4/GAG complexes are attached to a solid surface via a covalent bond between PF4 and the solid surface. FIG. 1C shows a method in which heparin is randomly cross-linked to a solid surface before addition of PF4. FIG. 1D shows the method of the present invention in which the GAG is attached at one end (unidirectionally) to the solid support before the addition of PF4. FIG. 1E shows the naturally occurring situation where platelet factor 4 interacts with GAG molecules displayed on vascular endothelial cells. This display occurs in the form of a "proteoglycan" molecule consisting of a protein backbone to which multiple GAG molecules are attached by ester linkages to serine groups (Ihrke, supra, 1994).

FIG. 3 is a diagram of the various monosaccharide building blocks identified in heparin.

FIG. 5 compares the amino acid sequence of human (HPF4), rat (RPF4), and bovine (BPF4) platelet factor 4. The amino acid sequence of the HPF4 has been numbered for the mature form (without the signal peptide) of the protein as secreted in the recombinant *E. coli* expression system.

DETAILED DESCRIPTION OF THE INVENTION

A. In General

Platelet-activating, heparin-induced antibodies are specific for PF4/GAG complexes. In the present invention, the complexes are immobilized on a solid support, such as a microtiter plate well, and detected, preferably using colormetric techniques. The present invention provides a new approach for detection of HITP antibodies which involves: 1) treatment of commercially available heparin or other glycosaminoglycan (GAG) with nitrous acid to produce fragments of various sizes, each of which has a reactive aldehyde (CHO) group at its reducing terminal residue, 2) dialysis of the GAG digest to remove low molecular weight fragments, 3) covalent linkage of the CHO groups on the remaining, larger fragments to the surface of a solid support by reductive amination (see FIG. 2), 4) addition of purified PF4, preferably native human PF4, which binds spontaneously to the immobilized GAG molecules by virtue of its net positive charge, 5) addition of serum or plasma from a patient with HITP antibody, and 6) detection of antibody bound to the target heparin/PF4 complexes with a suitable antibody-specific probe.

B. Attachment of GAG to a Solid Support

1. Attachment Process

Figure 1A:
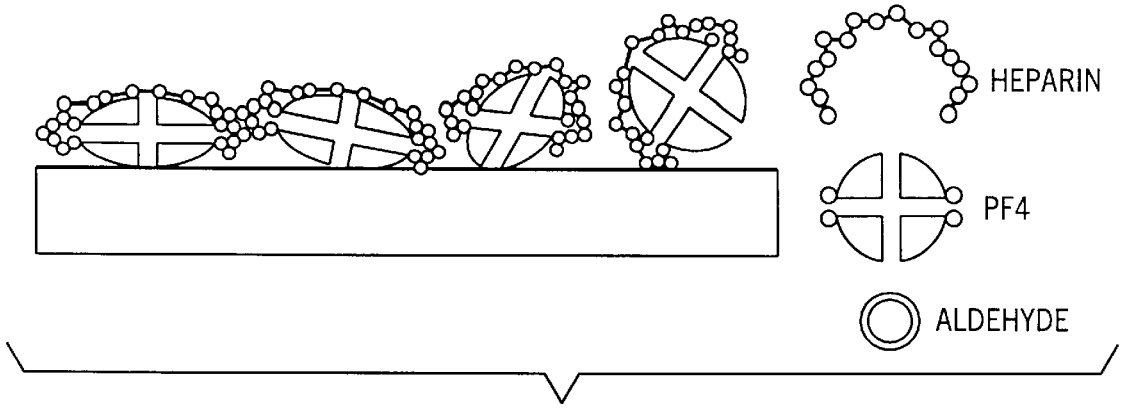
FIGS. 1A–E describes four methods of attaching a glycosaminoglycan, such as heparin, and PF4 to a solid support.

A prerequisite for detection of HITP antibodies is the availability of target complexes consisting of human PF4 complexed with a GAG, such as heparin. Heparin/PF4 complexes can be immobilized on a solid surface by several different methods. Four approaches are shown schematically in FIG. 1. FIG. 1A diagrams the method of Amiral and coworkers who first described detection of HITP antibodies using heparin/PF4 complexes (J. Amiral, *Thromb. Haemostasis* 68: 95, 1992). This disclosure describes the use of heparin/PF4 complexes (formed at a ratio of 0.25 U/ml heparin and 20 µg/ml PF4) immobilized by adhesion to "micro-ELISA" plates. The heparin/PF4 complexes are formed before attachment to the plates.

Figure 1B:
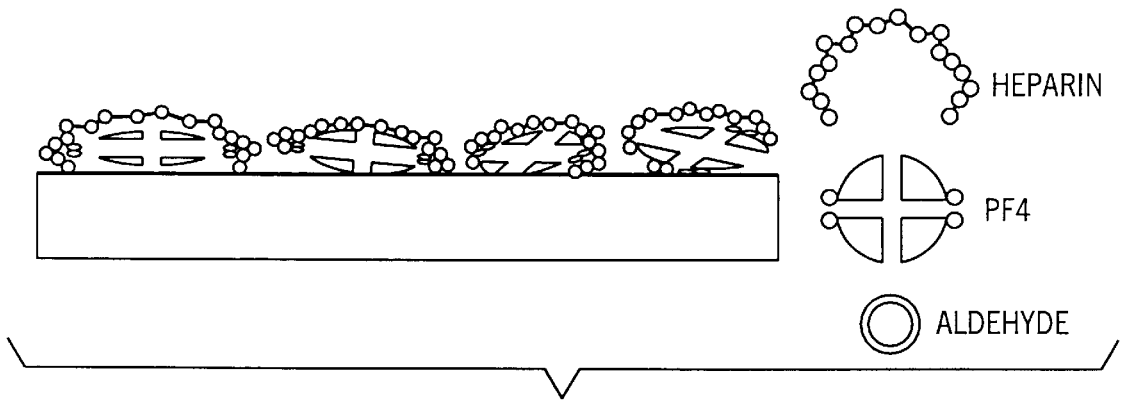

FIG. 1B diagrams a second method of immobilizing heparin/PF4 complexes. A. Greinacher, et al. (*Thromb. Haemost.* 71: 247, 1994) detected HITP antibodies with immobilized PF4:heparin complexes formed at a ratio of 0.5 U/ml heparin: 20 µg/ml PF4. The PF4 in these complexes was covalently coupled to microtiter plates using Covalink plates (manufactured by Nunc, Roskilde, Denmark) activated with M-maleimidobenzoyl-N-hydroxy-sulfo-succinimide ester.

Figure 1C:
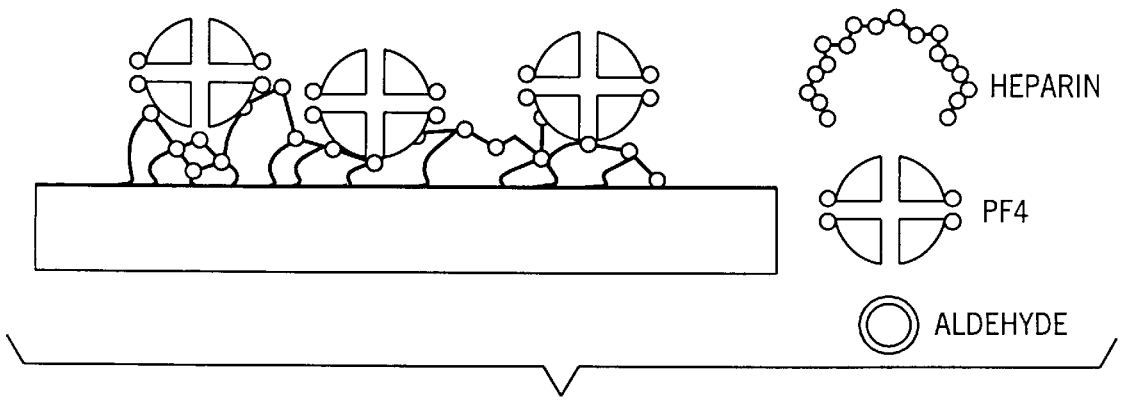

Heparin and other GAGs can be linked covalently to a solid surface (as illustrated in FIG. 1C) by several other methods. These include coupling to cyanogen bromide-activated polyvinyl alcohol (G. Schmer, Trans. Amer. *Soc. Rtif. Int. Organs* 18: 321, 1972) and linkage to cyanuric chloride-activated agarose (Finlay, et al., *Analyt. Biochem.* 108: 354, 1980). Alternatively, the carboxyl groups of heparin can be activated by carbodiimide and coupled to an aminated polymer. (I. Danishefsky, et al., *Thromb. Res.* 4: 237, 1974) or aldehyde functions can be introduced into the heparin polymer by partial oxidation with sodium periodate and these can be coupled to an aminated surface by reductive amination (D. D. Solomon, et al., Trans. 10th *Europ. Cong. Biomaterials,* 1986, Abstract 209). Each of these methods leads to cross-linkage of the heparin chain to the solid surface at multiple points, in contrast to the method of the present invention in which each GAG molecule is linked to the solid surface only by a single covalent bond formed at the reducing end of the molecule. We refer to the FIG. 1C method as the "cross-linking" method because the heparin is cross-linked to the solid support at numerous points.

Preformed heparin/PF4 complexes immobilized in microtiter plates as described by Amiral, et al. (supra) (FIG. 1A), Greinacher, et al. (supra) (FIG. 1B) and the FIG. 1C method are suboptimal for HITP antibody detection for several reasons. First, the PF4 molecule is deformed or denatured upon binding to plastic (FIGS. 1A and 1B), especially if the PF4 is covalently linked to the solid surface (FIG. 1B). The potential adverse consequences of this denaturation on antibody detection are illustrated by the recent finding of Visentin, et al. that HITP antibodies recognize subtle conformational or combinatorial epitopes created by the binding of heparin to selected amino acid sequences present in the human PF4 molecule, but absent in PF4 from other species (G. P. Visentin, et al., Blood 84(Suppl. 1): 246a, 1994b). Second, plasma from some patients contains antibodies that bind to PF4 alone when it is immobilized by adhesion to plastic microtiter wells (Visentin, et al., supra, 1994a). When present, these antibodies increase background and impede the detection of antibodies reactive with heparin/PF4 complexes.

Figure 6:
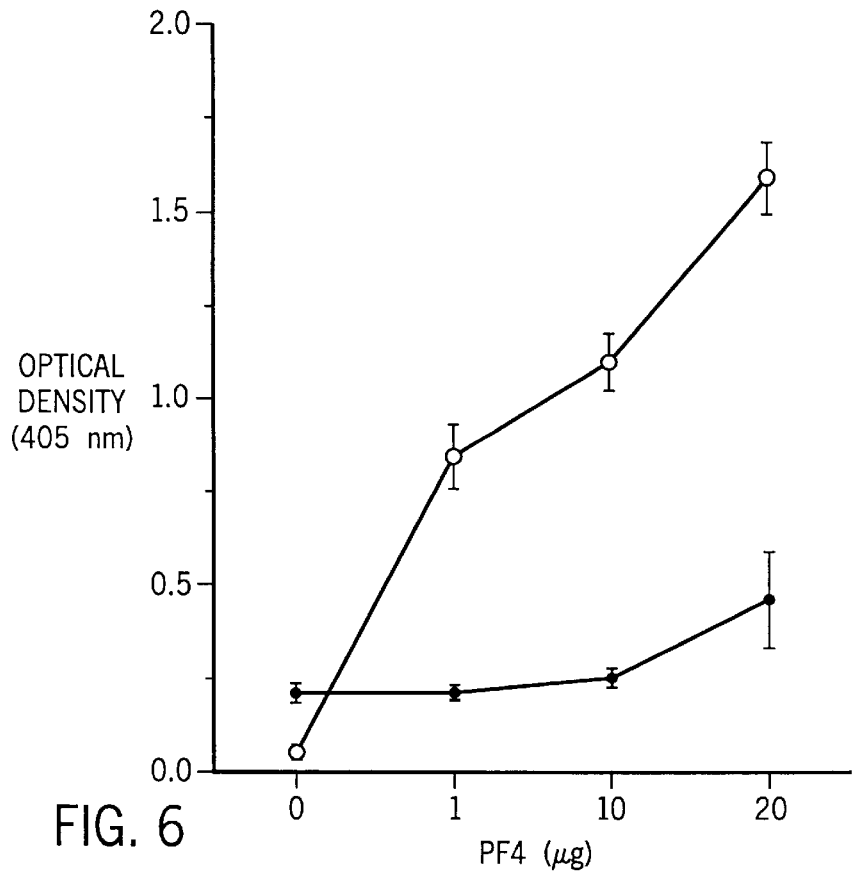
FIG. 6 compares the reaction of HITP antibodies against immobilized heparin/PF4 complexes prepared by the method of the present invention and by the "cross-linking" method described below.

Second, background optical density (OD) measurements obtained with normal control sera in the systems of Amiral, et al., supra and Greinacher, et al., supra were high. Thus, "positive" reactions were defined as those with OD>0.5 (Amiral, et al., supra) and >0.2 (Greinacher, et al., supra) The background optical density (OD obtained with normal serum in the presence of PF4 or patient serum in the absence of PF4) is also greater than 0.20 using the cross-linking method (FIG. 1C and described in Example 7 and FIG. 6 below). In contrast, the background OD for the method of the present invention is less than 0.05 (see Example 7 and FIG. 6).

The higher background ODs of the prior art methods are due in part to deformation of the PF4 molecule caused by its adhesion or covalent linkage to the plastic surface. The lower background OD intrinsic to the method of the present invention allows weaker antibodies to be detected more readily.

Figure 1D:
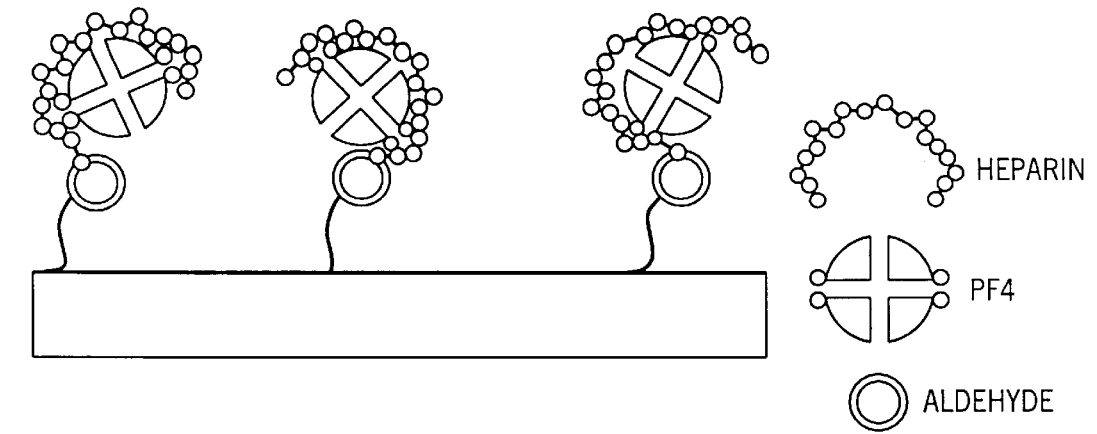
Figure 1E:
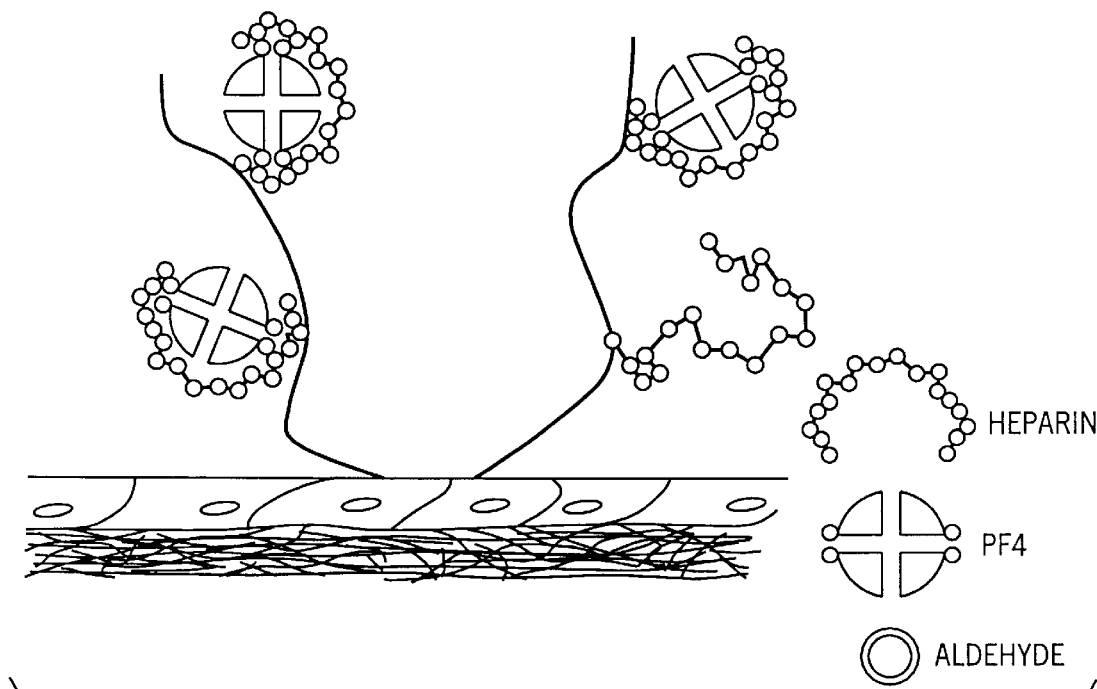

As illustrated in FIG. 1D, the method of the present invention enables the formation of heparin/PF4 complexes similar to those formed when PF4 interacts with GAG molecules displayed on vascular endothelial cells (FIG. 1E) (Visentin et al., supra, 1994a) while minimizing contact between the PF4 molecule and the surface on which the heparin is immobilized and avoiding deformation of the PF4.

Figure 7:
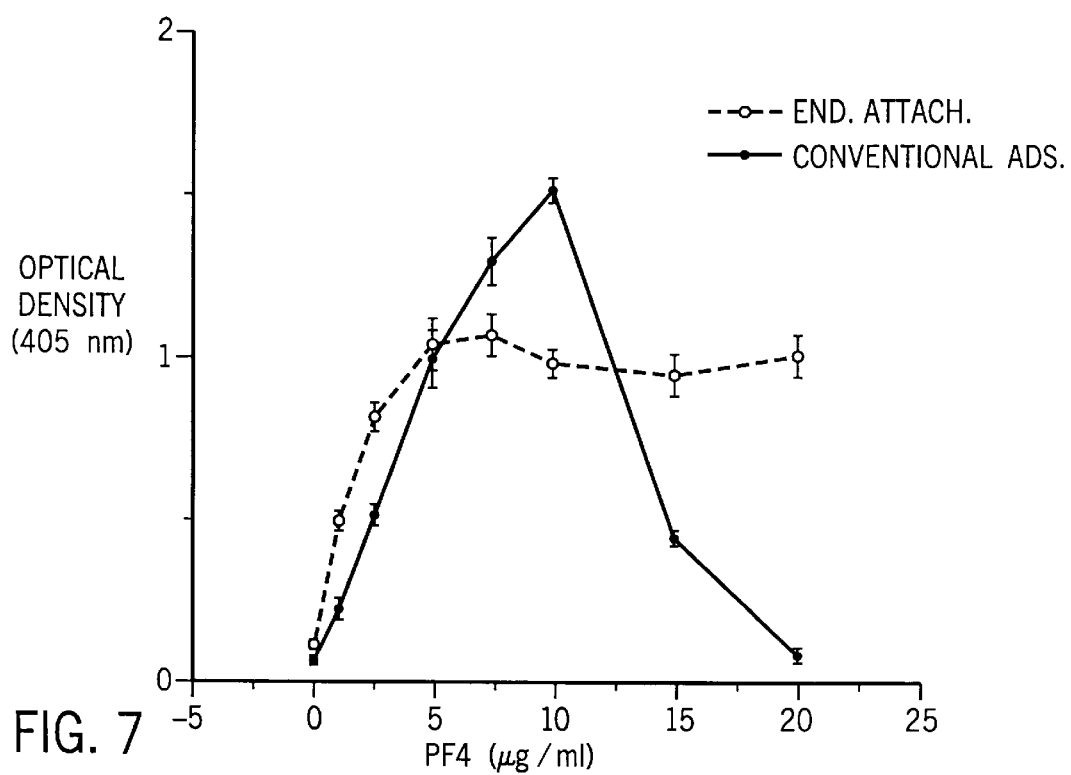
FIG. 7 compares the ratio of heparin/platelet factor 4 necessary for platelet factor 4 binding to 1) heparin unidirectionally attached to plates before exposure to platelet factor 4 and 2) heparin/platelet factor 4 combined before being adhered to a solid support.

A further advantage of the method of the present invention is that the ratio of PF4: heparin is not critical. (see FIG. 7, below) In fact, best results are obtained when an immobilized GAG, such as heparin, is saturated with added PF4. In contrast, using the methods described in FIGS. 1A or 1B, only heparin/PF4 complexes formed at certain ratios of the two reactants are able to bind HITP antibodies (Visentin, 1994a).

Figure 2:
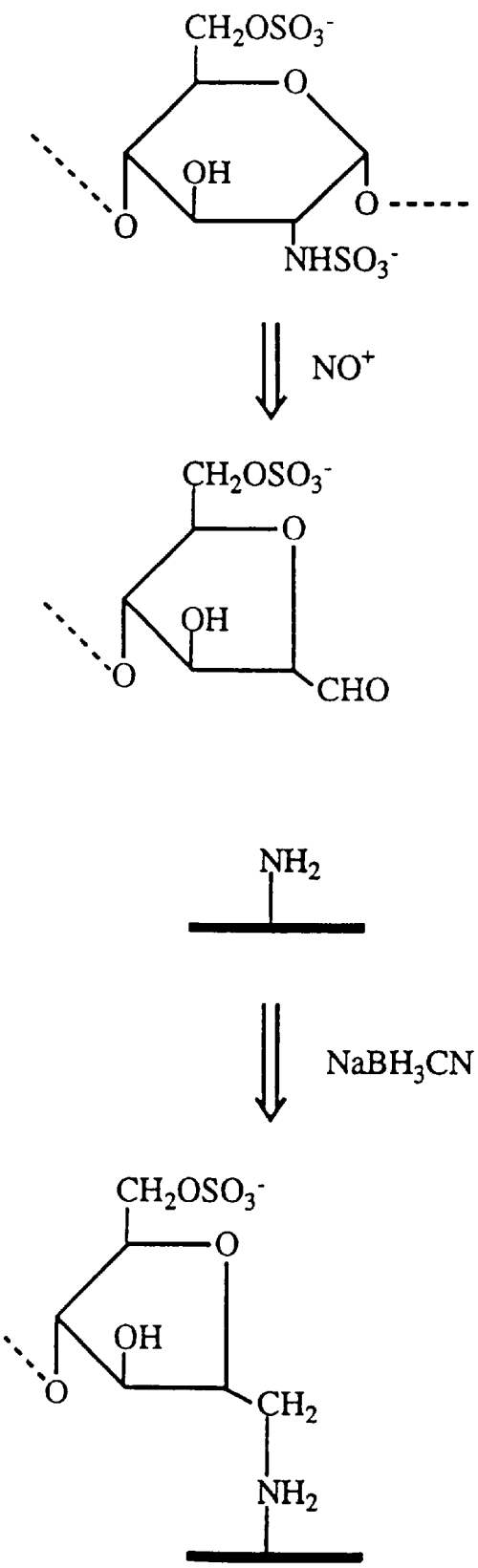
FIG. 2 is a scheme for nitrous acid fragmentation of heparin and coupling of the fragments to an aminated surface by reductive amination.
Figure 3B:
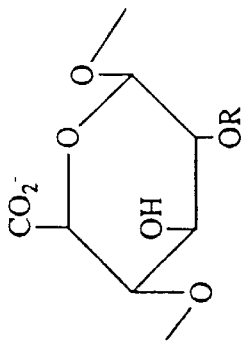
FIG. 3A and 3B are uronic acid residues.
Figure 3D:
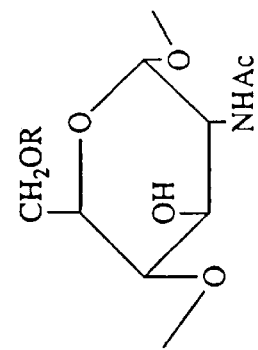
FIG. 3C and 3D are glucosamine residues.
Figure 3A:
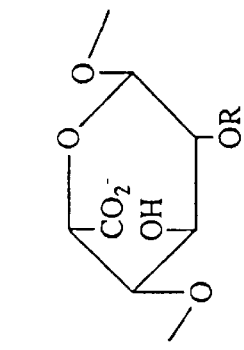
Figure 3C:
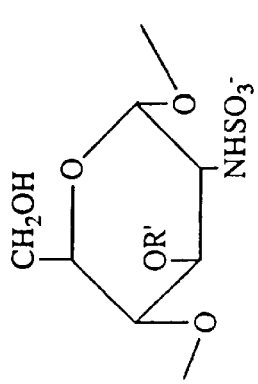

To practice the method of the present invention, one would first attach a suitable GAG molecule at its reducing end (unidirectionally) to a solid support, such as a microtiter plate well or bead. Suitable GAGs are discussed below. Before attachment the GAG molecules are typically fragmented, preferably by nitrous acid. FIG. 2 is a schematic diagram of nitrous acid fragmentation and the subsequent attachment of the GAG molecules to a solid support.

Additionally, V. D. Nadkarni, et al., *Anal. Biochem.* 222: 59–67, 1994, describes three other ways in which heparin can be attached unidirectionally to a solid surface through the reducing end of the molecule. These methods, although more complex than the method used in the Examples, would also be suitable.

Nadkarni, et al. describes 1) modification of the reducing end to form 2,6-diamino pyridinyl heparin containing a reactive amino group; 2) synthesis of omega-hydrazidoadipyl-azo heparin containing a hydrazide group and 3) synthesis of heparin lactone containing a reactive ester group (V. D. Nadkarni, et al., supra, 1994).

Each of these methods allows coupling of the heparin molecule at one end to a solid support so as to mimic its orientation in the naturally occurring proteoglycan (FIG. 1E), leaving practically all the binding sites on the heparin molecule free to interact with platelet factor 4. Heparin immobilized by these methods binds about six times as much of the heparin-binding protein, protamine (per mg of heparin), as commercially available heparin SEPHARROSE resin CL-6B (to which heparin is cross-linked at multiple sites (Nadkarni, supra, 1994). This difference reflects full availability of binding sites on the extended heparin chain, in contrast to the limited availability of these sites on heparin cross-linked nondirectionally to a surface at multiple sites.

Casu, et al. ("Methods of Structural Analysis" in *Heparin: Chemical and Biological Properties, Clinical Applications*, D. A. Lane and U. Lindahl eds., CRC Press, Inc., Boca Raton, Fla., 1989) describes three ways in which the heparin chain can be cleaved to produce random fragments. Cleavage according to the method of the present invention (nitrous acid digestion) leaves a unique aldehyde group at the end of each fragment. This enables unidirectional immobilization of the molecule by reductive amination. Fragmentation of heparin by the other two methods described by Casu (treatment with heparinase and Smith degradation) fails to produce fragments that have a unique chemical group at one end of the molecule. Fragments produced by the latter methods cannot be immobilized unidirectionally and are not suitable for the present invention.

Example 7 below describes an appropriate fragmentation of GAG molecules, in this case heparin molecules. In brief, heparin is dissolved in water with pH adjusted to 2.5. A solution of sodium nitrite in 1 ml of water is added dropwise. The reaction mixture is stirred at room temperature for 2 hours. The pH is then adjusted to neutrality with sodium hydroxide.

This mixture is then dialyzed through a 3 kDa cutoff membrane against distilled water. The end product is preferably filtered through a 0.2 micron filter and stored at 4° C. The aliquot may be freeze-dried for long term storage. GAG fragments of between 3 kDa and 15–30 kDa are the preferred result of this fragmentation.

The fragmented GAG may be attached to an aminated surface by reductive amination. Once again, Example 7 describes an appropriate procedure for reductive amination. In general, one would take an alkylamine coated surface, such as beads or microtiter wells, and add the nitrous acid-treated GAG. Preferable alkylamine residues have a 6 carbon spacer arm and a terminal amino group. However, other alkylamine residues would be suitable.

Aminated surfaces suitable for the type of coupling outlined above include derivatized polystyrene beads (alkylamine beads from Pierce) and diaminodipropylamine-agarose (from Pierce). These matrices carry spacer arms of 6 and 9 residues, respectively, with a terminal amino group.

Preferably, one would add 4 ml of PBS (phosphate buffered saline) containing 36.9 mg of sodium cyano-borohydride to 25 ml (preferably 369.25 mg) of nitrous acid-treated GAG. The volume of this reaction is typically brought up to 50 ml by adding 21 ml of PBS. For this particular reaction volume, 14 alkylamine beads are added and the mixture is incubated on a rotor for 2 hours. Sodium cyano-borohydride (NaBH$_3$CN) is used to reduce the terminal aldehydic group of heparin, this converts the labile Schiff base formed between the aldehyde and the amino group to a stable covalent linkage. The beads are then typically washed 3 times using phosphate buffered saline (PBS—0.02M, pH 7.2) with 0.05% Tween-20 (TW) and then blocked with 20% fetal bovine serum (FBS) in PBS-TW for 30 minutes.

Another example is the use of diaminodipropylamine-agarose gel. Preferably, 1 ml of packed gel is combined with 12–15 mg of nitrous acid-treated GAG in 3 ml of PBS (at pH 5.8) containing 3 mg of sodium cyano-borohydride (NaBH$_3$CN) and incubated for 4 hours at room temperature. After three washes in PBS 0.5–0.7 mg of PF4 in 1 ml of PBS is added and the mixture is incubated at room temperature for 1 hour, then washed 3 times using PBS-Tw and blocked for 30 minutes with PBS-Tw-FBS (20%). The blocking step is not critical using this method since non-specific binding is virtually absent.

The solid support need not contain free amino groups. Other groups could be used to link the digested heparin and the solid support. For example, biotin-LC-hydrazide is a reagent that is available commercially at low cost. Streptavidin could be immobilized on microtiter plates. Added biotin-LC-hydrazide would bind tightly to the avidin, leaving the LC-hydrazide oriented away from the solid surface. Heparin fragments generated by nitrous acid digestion could then be coupled to the hydrazide groups. PF4 can then be added to produce targets for HITP antibody detection. Example 7, below, describes the attachment of GAG molecules to a solid support using this technique.

The solid support must be capable of binding the GAG compounds described below and the GAG/PF4 complex. Examples of such solid supports include hydrocarbon polymers such as polystyrene, polyethylene and polybutylene. Other suitable organic polymers include polyesters and polyamides, cellulose and cellulose derivatives, vinyl polymers and the like.

The overall reaction between the GAG molecules and solid support can be summarized as follows:

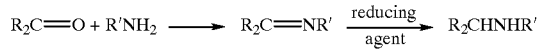

R$_2$=GAG, such as heparin and R'=spacer arm linking NH$_2$ group to solid surface.

2. Suitable Molecules for Attachment to the Solid Support.

We envision that glycosaminoglycan (GAG) molecules are suitable for attachment to solid support according to the method of the present invention. By "glycosaminoglycan" or "GAG" we mean "any of several high molecular weight linear heteropolysaccharides having disaccharide repeating units containing an N-acetyl-hexosamine and a hexose or hexuronic acid; either or both residues may be sulfated. This class of compounds includes the chondroitin sulfates, dermatan sulfates, heparan sulfate and heparin, keratan sulfates, and hyaluronic acid. All except heparin occur in proteoglycans." (definition from *Dorland's Illustrated Medical Dictionary*, 27th Ed., W. B. Saunders, Co., 1988).

A preferred GAG is heparin. By "heparin" we mean "a family of polysaccharide species whose chains are made up of alternating 1-4-linked and variously sulfated residues of a uronic acid and D-glucosamine" (B. Casu, in *Heparin: Chemical and Biological Properties; Clinical Applications*, D. A. Lane and U. Lindahl eds. CRC Press, Inc. Boca Raton, 1989, p. 25). Monosaccharide molecules identified to date in various heparins are shown in FIG. 3 (taken from B. Casu, 1989, p. 26, see above). The uronic acid residues can be either L-iduronic acid or D-gluconuronic acid; the D-glucosamine residues can be either N-sulfated or N-acetylated.

Figure 4A:
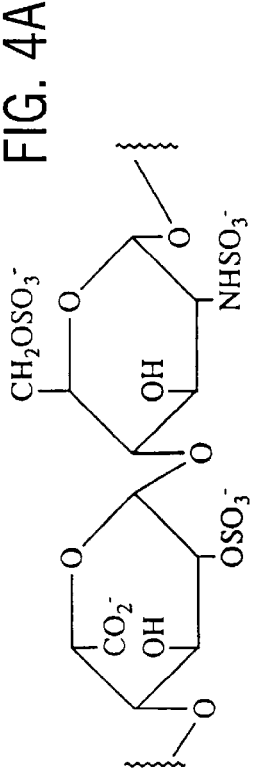
FIG. 4 is a diagram of typical heparin sequences.
Figure 4B:
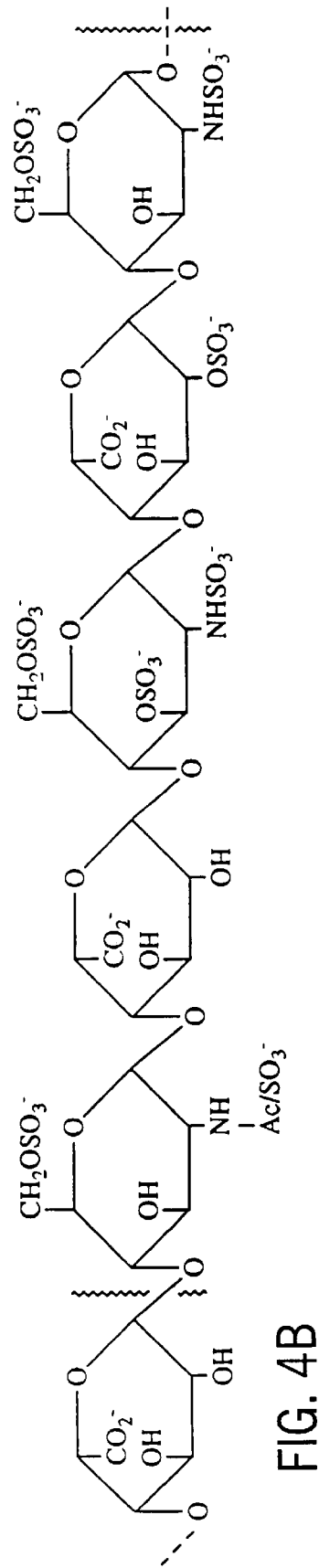
Figure 4C:
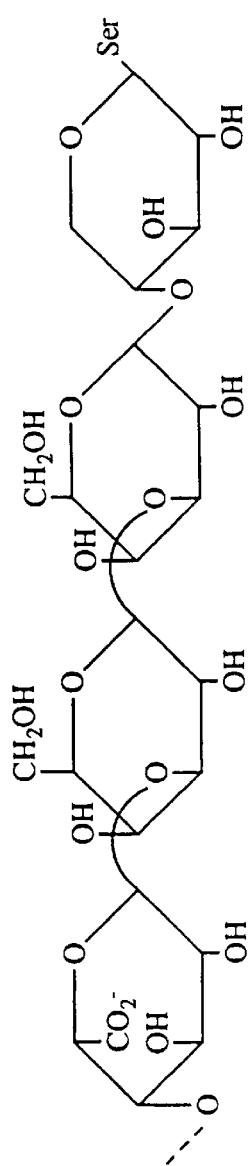

Typical heparin sequences are shown in FIG. 4 (also from B. Casu, 1989, see above). The sequence designated "A" is the major product of heparin biosynthesis and makes up about 90% of the structure of beef lung heparins and 70% of the structure of heparins from pig intestinal mucosa. Certain regions of heparin contain the pentasaccharide sequence "B" indicated in FIG. 4. This pentasaccharide sequence binds specifically to a defined region of "antithrombin III," a regulatory protein, to cause conformational changes that enhance its ability to inhibit activated clotting factors such as factor Xa and thrombin (factor IIa). This pentasaccharide sequence, which is responsible for much of the anticoagulant effect of heparin, is found in only a minority of the saccharide chains present in commercial heparin and is not essential for PF4 binding. Commercially available heparin preparations generally contain polysaccharide fragments ranging in molecular weight from 3,000–30,000 kD (U. Lindahl, in Lane and Lindahl, 1989, p. 161) with an upper limit of about 80,000 kD.

In mammals, heparin is found mainly in lung, intestine, liver, skin, and other tissues, but there is considerable species-to-species variation (from H. B. Nader and C. P. Dietrich, Lane and Lindahl, p. 84). Almost all tissue heparin is located in the metachromatic granules of mast cells (tissue basophils). A few species, e.g., rabbits, lack heparin altogether, suggesting that the physiologic role of heparin is unrelated to its function as an anticoagulant. Several studies have suggested that heparin is protective against infection by bacteria and viruses (e.g., W. Regelson, *Advances in Chemotherapy* 3: 303–370, 1968).

In medicine, heparin is used for the treatment and prevention of thrombosis. As noted above, its action involves inhibition of activated clotting factors, most importantly, thrombin (Factor IIa) and Factor Xa. These effects appear to be mediated by a subfraction of heparin with high affinity for antithrombin III. Heparin molecules with low affinity for antithrombin III can, however, bind to a structurally related protein, heparin cofactor II, to form a complex that inactivates thrombin (IIa) specifically. The latter reaction may also contribute to the anticoagulant action of heparin (D. M. Tollefsen, Lane and Lindahl, 1989, p. 257).

Chemically synthesized heparin fragments containing a defined number of saccharide residues are also envisioned to be suitable for the present invention. For example, heparin fragments of greater than 10 saccharide residues, and preferably between 10 and 20 saccharide residues, are envisioned to be especially preferred.

If one wished to evaluate whether a specific GAG or GAG fragment preparation is suitable for the present invention, one could repeat the experiments described in Example 7 with the candidate preparation. A heparin-induced antibody binding efficiency of at least 50%, and preferably 80%, of that shown in Example 7 will indicate that the fragment preparation is suitable.

A preferred heparin preparation is derived from porcine intestinal mucosa (Sigma Co., St. Louis, Mo.) and stored according to manufacturer specifications.

Heparan sulfate is also a preferred GAG. Heparan sulfate, like heparin, is made up of repeating disaccharide units consisting of variously sulfated D-glucosamine and hexuronic acid. A major difference between the two molecules is that heparan sulfate contains more than 20%N-acetylated glucosamine and fewer O-sulfate than N-sulfate substitutions (L. A. Fransson, Lane and Lindahl, 1989, p. 115). In mammals, heparan sulfate, in contrast to heparin, is found linked to a protein core, forming a family of molecules designated "proteoglycans." Proteoglycans containing heparan sulfate are found on the surface of practically all adherent mammalian cells (M. Hook, et al., *Annual Rev. Biochemistry* 53: 847, 1984). A number of different "core" proteins are recognized to which one or more heparan sulfate molecules are linked to form the mature proteoglycan.

Other naturally occurring heparin-like glycosaminoglycans which are suitable for the present invention include chondroitin sulfate, dermatan sulfate, keratan sulfate, and hyaluronic acid. A typical synthetic glycosaminoglycan is dextran sulfate.

C. Addition of Platelet Factor 4 to the Solid Support

In its natural state, platelet factor 4 is a tetramer with a molecular weight of approximately 32,000 daltons (see Ryo, et al., *Thromb. Res.* 17: 465–652, 1980; Zucker, et al., *Proc. Soc. Exp. Biol. Med.* 198: 693–702, 1991, for a full description of PF4). The PF4 used in the method may be PF4 derived from human platelets, recombinant human PF4 (from Dr. Poncz, University of Pennsylvania, Philadelphia, Pa.) or human PF4 manufactured by standard peptide synthesis. SEQ ID NO:1 is the amino acid sequence of a typical human PF4 (from Poncz, et al., *Blood* 69: 219–223, 1987.

The PF4 derived from platelets is typically obtained by pooling platelets from whole blood donors in a suspension and releasing PF4 by adding thrombin-receptor activating peptide (TRAP 11). (T. K. H. Vu, et al., *Cell* 64: 1057–1068, 1991; T. K. H. Vu, et al., *Nature* 353: 674–677, 1991.) This method causes the release of platelet alpha granule constituents, including PF4, without release of other proteins, providing a significant purification of PF4 in only one step. This procedure is described in detail in Example 2.

In place of whole PF4, a peptide fragment or fragments having amino acid sequences found in human PF4 may be substituted. Furthermore, a peptide capable of binding to a GAG such as heparin to form an epitope recognized by antibodies generated in an HITP immune response may be substituted for PF4 in the methods described.

To determine whether a candidate PF4 fragment or a peptide is suitable for the present invention, one would perform a comparison between the candidate peptide and native PF4. An efficacy of binding HITP-generated antibodies of at least 50% that of native PF4 would indicate that the fragment was suitable for the present invention.

Platelet factor 4 is added to the GAG-solid support combination by the following method:

PF4 in PBS is added at a saturating concentration. In a specific example: 1 ml of packed diaminodipropylamine-agarose beads is coupled to 12–15 mg of nitrous acid-treated GAG. Subsequently, 0.5–0.7 mg of PF4 is added and binds to the GAG-coated agarose beads. Heparin bound to the solid phase is quantitated on the basis of its capacity to bind toluidine blue (P. K. Smith, et al., *Analytical Biochemistry* 109: 466–473, 1980). The suitability of the final preparation for HITP antibody detection is assessed by the binding of well-characterized HITP antibodies (positive control).

D. Patient Samples

Blood plasma or serum is obtained from a patient suspected of having HITP. We envision that both human and animal patients will be successfully diagnosed. Preferably, 0.2 ml is needed for a test reaction.

It is an advantage of the method of the present invention that either serum or plasma can be used as the source of HITP antibody without concern for its PF4 content. In the method of the present invention, unidirectionally immobilized heparin molecules are saturated with platelet factor 4 to provide targets for HITP antibody detection. Thus, PF4 normally present in serum, ranging from 1 to 10 $\mu$g/ml (Visentin, et al., *J. Clin. Invest.* 93: 81–88, 1994) does not affect the sensitivity of the assay. In contrast, when heparin is not covalently linked to the solid surface (as in FIGS. 1A and 1B), PF4 added with serum can strip heparin from the surface, thus reducing significantly the sensitivity of the assay for detection of HITP antibodies contained in the same serum.

Small amounts of residual heparin present in serum or plasma to be tested for HITP antibodies can interfere with antibody detection by stripping PF4 from the target heparin: PF4 complexes prepared by any of the methods shown in FIG. 1. Because samples for testing are often obtained from patients who recently received heparin, it is not uncommon for residual heparin to be present. It is preferable that this residual heparin be removed by absorption with Ecteola cellulose or a similar agent to achieve maximum sensitivity for antibody detection. The blood plasma may absorbed with Ecteola cellulose (epichlorohydrin triethanolamine cellulose) to remove traces of residual heparin (A. R. Thompson, et al., *J. Lab. Clin. Med.* 88: 922–929, 1976, G. P. Visentin, et al., 1994, supra).

The sample is preferably diluted to a ratio of 1:10 V/V or more before being added to each of the microtiter plate wells. The plates are typically incubated at room temperature for a period of time, preferably 1–2 hours.

E. Quantitative Determination

Quantitative determination is obtained by contacting the coated solid support with a labeled material. The labeled material used in the immunoassay may be any conventional enzyme covalently linked to an immunological component known to the art. Enzymes suitable for use with the present invention include catalase, peroxidase, urease, glucose oxidase and alkaline phosphatase.

The substrate selected to react with the enzyme can be acted upon by an enzyme to produce a reaction product. Where alkaline phosphatase is the enzyme, a preferred substrate is PNPP (P-nitrophenyl phosphate). The reaction product generated by the action of alkaline phosphatase on PNPP is p-nitrophenol, a yellow substrate that can be measured spectrophotometrically at 405 nM. (S. L. Snyder, et al., *Biochem. Biophys.* Acta 258: 178–187, 1972). Other substrates suitable for use with alkaline phosphatase include 4-methyl umbelliferyl phosphate, alpha-napthyl phosphate, flavone-3-diphosphate and thymolphthalein.

The amount of substrate reaction product and the intensity of color produced will be direct functions of the amount of enzyme conjugate bound to the support plate. Therefore, a measure of substrate reaction product is a measure of the heparin-induced antibody which has been bound to the solid support. The measure is determined by obtaining an optical density (OD) of the reaction product formed on the solid support. The OD of an unknown plasma or serum is contrasted with a control OD determination of a known normal plasma or serum as part of the described assay. If the OD readings are substantially the same, the suspect plasma/serum will not contain antibody to the complex. However, if the suspect plasma/serum OD reading is at least 3× the normal reading, the plasma/serum donor has HITP or is at risk of developing it.

Other methods are suitable for the detection of HITP antibodies bound to GAG/PF4 complexes. In one method, red blood cells (or other particles) are coated with polyclonal or monoclonal antibodies specific for human IgG, IgM, or IgA. Adhesion of these red cells to complexes consisting of HITP antibody bound to immobilized GAG/PF4 complexes is then utilized to indicate the presence of bound HITP antibody (Y. Shibata, et al., *Vox Sang* 41: 25–31, 1981).

Alternatively, latex particles or other particulate material can be coated with GAG/PF4 complexes using the method of the present invention, and HITP antibodies can be detected by their ability to promote agglutination of these coated particles, either directly or after addition of a secondary anti-immunoglobulin reagent. Beads coated with GAG/PF4 may be used to detect HITP antibodies in a flow cytometric assay.

F. Diagnostic Kit

Diagnostic applications may be implemented according to the present invention in the form of a kit containing complexes which undergo a reaction with a sample of a patient's blood. The kit includes a solid support, such as a microtiter tray, containing wells coated with the glycosaminoglycan/PF4 complex by the method described above.

The desiccated complexes can be stored for a long period of time, at least 6 months. The kit preferably includes a receptacle containing a chemical label, such as alkaline phosphatase-labeled, goat anti-human IgG (H+L), mouse anti-human IgG, IgA, and IgM and a receptacle containing a suitable substrate, such as p-nitrophenyl phosphate.

A receptacle containing Ecteola cellulose for removing residual heparin may also be included.

EXAMPLES

In General

The present invention is further described by reference to the following, illustrative examples. The contents of the publication by Visentin, et al., *J. Clin. Invest.* 93: 81–88, 1994, are hereby incorporated by reference. The Examples utilize plasma samples from 12 patients who developed thrombocytopenia with or without thrombosis while receiving heparin therapy and whose plasma had tested positive in the serotonin release test for heparin-induced antibodies. The samples were collected within two days after heparin treatment was discontinued. The patients ranged in age from 51 to 75 years. Each plasma sample was adsorbed with Ecteola cellulose equilibrated in PBS (from Sigma Chemical Company, St. Louis, Mo.) to remove residual heparin that might be present. Seventy mg ecteola to 1 ml of plasma was incubated for 90 minutes at 4° C. with occasional agitation and was centrifuged at 14000 g for 1 minute.

Examples 1 and 2 describe the isolation of platelets and the purification of platelet factor 4. Example 3 describes the serotonin release assay for heparin-induced antibodies and serves as a comparison to the method of the present invention. Examples 4 and 5 describe an ELISA assay conducted with PF4/heparin complexes formed before being immobilized. These Examples are not by the method of the present invention but were performed in order to characterize heparin-induced antibody binding to the PF4/heparin complex by prior art methods. Example 6 is a characterization of complexes containing PF4 and peptides derived from PF4. Example 7 describes the method of the present invention in which a GAG molecule is attached unidirectionally at one end to a solid support and subsequently forms a complex with platelet factor 4.

Example 1

Isolation of Platelets

Platelets were isolated from freshly collected blood anticoagulated with acid citrate dextrose sufficient to produce a pH of 6.4–7.2, with an optimum pH of 6.5, and were washed once in RCD buffer (Ringer's citrate dextrose containing 0.108 mol/liter NaCl 0.038 mol/liter KCl, 0.0017 mol/liter $NaHCO_3$, 0.0212 mol/liter $Na_3C_6H_5O_7$. $2H_2O$, 0.0278 mol/liter $C_6H_{12}O_6$, 0.011 mol/liter $MgCl_2O.6H_2O$) at pH 6.5 (6.4–7.2) containing 50 ng/ml $PGE_1$ (from Sigma Chemical Company, St. Louis, Mo.).

Example 2

Purification of PF4

PF4 was purified according to Medici, et al., *Thrombo. Res.* 54: 277–287, 1989, the contents of which are hereby incorporated by reference, with minor modifications. 10 U of platelets (aged less than or equal to 1 day old) from randomly chosen whole blood donors was pooled. The platelet-rich plasma was pelleted at 1200 g, washed once in RCD buffer at a pH of 6.5 (6.4–7.3) containing EDTA, 0.002 M, and resuspended in PBS (buffer containing 0.02 M/liter, pH 7.2 with 0.145 M/liter NaCl) containing 0.001 M $CaCl_2$, and 0.0014 M PMSF phenyl methyl sulfonyl fluoride (from Sigma Chemical Company, St. Louis, Mo.) in dimethyl sulfoxide at a concentration of $10^{10}$ platelets/ml in a total volume of 50 ml.

PF4 release was induced with TRAP 11 (thrombin receptor activating peptide) (Peptide Core Lab, Blood Research Institute, Milwaukee, Wis.) at a final concentration of 5 $\mu$M for 10–20 minutes at 37° C. with occasional shaking. The activated platelets were then pelleted at 3000 g for 30 minutes at 4° C. (2–8° C.). Ammonium sulfate was slowly added to the supernatant at 60% saturation and the mixture was incubated at 4° C. (2–8° C.) overnight (4–16 hours). The precipitate was discarded and the final supernatant was dialyzed against PBS at 4° C. The dialyzed supernatant (approximately 250 ml) was then incubated with 10 ml of packed heparin-Agarose beads for 4 hours at 4° C. (2–8° C.) with gentle stirring. The beads were washed sequentially with three volumes each of 0.145 M PB-NaCl, 0.8 M PB-NaCl (to remove beta-thromboglobulin and thrombospondin) and resuspended in 10 ml of 1.6 M PB-NaCl to release bound PF4.

The final eluate was concentrated using Centriprep 10 (Amicon, Beverly, Mass.) to a 5-ml volume, dialyzed against PBS at 4° C. and treated for 1 hour at 4° C. (2–8° C.) with an excess (70 mg) of ecteola cellulose (from Sigma Chemical Corp., St. Louis, Mo.) equilibrated in PBS to remove residual anti-thrombin-III. The supernatant was then centrifuged and was shown to contain a single protein of approximately 7.8 kD using Coomassie blue stain after electrophoresis in a 5% SDS-polyacrylamide gel. The supernatant was stored in 0.0014 M PMSF and 0.05% sodium azide (from Sigma Chemical Company, St. Louis, Mo.).

Example 3

Serotonin Release

The serotonin release test was performed as described by Sheridan, et al., *Blood* 67: 27–30, 1986, with minor modifications, (see Tomiyama, et al., *Blood* 80: 2261–2268, 1992, the contents of which are hereby incorporated by reference). Washed platelets labeled with [$^{14}$C] serotonin were incubated with aliquots of patient plasma (recalcified and dialyzed) and 0.1 U/ml heparin in albumin-free tyrode's buffer containing 0.002 M $CaCl_2$ and 0.001 M $MgCl_2$ for 60 minutes at room temperature with gentle agitation. Release of serotonin at least 3 SD in excess of that obtained with normal plasma was considered positive.

The results of this assay are described at the end of Example 5.

Example 4

PF4/Heparin ELISA Enzyme Linked Immunosorbant Assay

A ratio of heparin/PF4 of 0.4 U/ml (0.2–0.6) heparin:10 mg/ml PF4 is required to produce complexes capable of binding heparin-induced antibodies when the heparin and PF4 are added together before being attached to a solid support. Fifty microliter aliquots of PF4 were mixed with heparin at various concentrations and incubated overnight (4–16 hours) at 4° C. (2–8° C.) in the wells of a polystyrene microtiter plate (Easy wash; Corning, Corning, N.Y.). The trays were washed three time with PBS-Tw (PBS with Tween-20, 0.05%) and blocked for 30 minutes at room temperature with PBS-Tw, FCS (from Hyclone Labs, Logan, UT) 20%. Fifty microliters of plasma diluted 1:10 or 1:50 in PBS was added to each well and incubated for 60 minutes at room temperature. After three washes with PBS-Tw, bound IgG and/or IgM was detected by adding alkaline phosphatase-labeled goat anti-human IgG and/or IgM diluted 1:1000 in PBS-Tw-FCS (10%), followed by incubation for 1 hour at room temperature, washing four times, and incubation with p-nitrophenyl phosphate substrate for about 1 hour (goat antihuman IgM and IgG, Zymed Labs, Inc., San Francisco, Calif. and Celsus Laboratories, Cincinnati, OH and Incstar Co., Stillwater, N. Mex.). The reaction was stopped with 1 N NaOH and absorbance was read at 405 nm using 650 nm for reference values. Reactions were considered positive when the mean optical density (OD) obtained with PF4/heparin complex was at least 3 SD greater than the value obtained with PF4 only, in the control wells.

Example 5

Analysis of ELISA Method

IgG bound readily to complexes formed in mixtures of 0.3 U/ml heparin and 10 μg/ml PF4 or 1.0 U/ml heparin and 25 μg/ml PF4. However, at a given concentration of heparin, doubling the PF4 concentration or reducing it by 50% led to a marked reduction of reactivity (G. P. Visentin, et al., *J. Clin. Invest.* 93: 81–88, 1994).

Plasma from 50 patients with other immune platelet disorders (19 with autoimmune thrombocytopenia, 14 with drug-induced thrombocytopenia, 6 with post-transfusion purpura and 11 women who had given birth to an infant with neonatal alloimmune thrombocytopenia) was also tested in the ELISA. Forty-seven of the 50 samples gave negative reactions for IgG antibody at 1:10 (V/V) dilution. The remaining three (two with post-transfusion purpura and one with autoimmune thrombocytopenia) gave positive reactions at 1:10 (V/V) but were negative at 1:50 (V/V) dilution. Reactions of the 12 HITP plasmas at various dilutions in the ELISA and in the serotonin release test are shown in Table 1. At a dilution of 1:100, only 2 samples gave positive serotonin release tests, but the ELISA was positive with all 12 at 1:200 and with nine at 1:500.

It is generally agreed that the serotonin release assay is more sensitive than the commonly used platelet aggregation test (see Warkentin, et al., *Prog. Hemostasis. Thromb.* 10: 1–34, 1991; Favoloro, et al., *Pathology* 24: 177–183, 1992). However, each of 12 plasmas containing heparin-induced antibodies gave positive reactions at a dilution of 1:200 and nine were positive at 1:500. Conversely, the serotonin release test provided positive results from only 2 plasmas at a dilution of 1:100 (V/V) and 0 at a dilution of 1:200 and 1:500 indicating a very sensitive microtiter tray ELISA (Table 1).

TABLE 1

Relative Sensitivity of the Serotonin Release and ELISAs for Detection of Heparin-induced (IgG) Antibodies in 12 Patients with HITP

| Assay | No. of Positive reactions | | | | |
|---|---|---|---|---|---|
| | Undiluted | 1:10 | 1:100 | 1:200 | 1:500 |
| Serotonin Release | 12 | 12 | 2 | NT | NT |
| ELISA | 12 | 12 | 12 | 12 | 9 |

NT = not tested

Example 6

Characterization of Complexes Containing PF4 and Peptides Derived from PF4

1. Structure of Human Platelet Factor 4 (PF4)

Human PF4 is a symmetrical tetrameric molecule made up of four identical subunits. Each subunit contains 70 amino acid residues, the sequence of which is known (M. Poncz, et al., *Blood* 69: 212, 1987). Each PF4 monomer contains an alpha helical structure at its C-terminus (X. Zhang, et al., *Biochemistry* 33: 8361, 1994). Lysine resides on the exterior face of each alpha helix are thought to be the major sites at which the negatively charged heparin molecule binds (J. Loscalzo, et al., *Arch. Biochem. and Biophys.* 240: 446, 1985). It is believed that a heparin molecule containing 18 saccharide residues can attach perpendicular to these alpha helical residues and span one-half of the tetramer (J. A. Stuckey, et al., *Proteins Structure, Funct. Genet.* 14: 277, 1992). Antibodies associated with heparin-induced thrombocytopenia/thrombosis (HITP) fail to recognize heparin alone or PF4 alone but bind avidly to the heparin: PF4 complex (G. P. Visentin, et al., *J. Clin. Invest.* 93: 81, 1994a). We postulate that these antibodies recognize combinatorial epitopes consisting partly of heparin and partly of PF4 at one or more positions where the molecules contact each other when the complex is formed. An alternative, but less likely possibility is that HITP antibodies recognize a conformational change elsewhere on the PF4 molecule that is created when the complex forms.

2. Preliminary Investigations

We have carried out a series of studies to identify the site or sites on the heparin/PF4 complex recognized by HITP antibodies. In one study, peptides consisting of the C-terminal 15 and 26 amino acids (major heparin-binding region) of human PF4 were synthesized. Using tritiated heparin, we found that only the 26-mer could bind heparin effectively. The 26-mer was complexed with heparin at a wide range of peptide:heparin ratios but when immobilized in microtiter wells, failed to bind any of a panel of HITP antibodies.

Human, rat, and bovine PF4 are about 74% homologous (FIG. 5). (Human PF4 is described at SEQ ID NO:1, rat PF4 is described at SEQ ID NO:2, and bovine PF4 is described at SEQ ID NO:3.) We purified rat and bovine PF4 and complexed these preparations with heparin at a wide range of PF4:heparin ratios. None of these PF4/heparin complexes bound any of a panel of HITP antibodies. Negative reactions were also obtained with the heparin-binding proteins beta-thromboglobulin and protamine.

Chimeric PF4 molecules consisting of N-terminal rat sequence and C-terminal human sequence and vice versa were then constructed and expressed in *E. coli*. The chimeric molecules formed tetramers and bound heparin efficiently. However, neither molecule was able to bind HITP antibodies when complexed with heparin.

These findings indicate that HITP antibodies recognize epitopes that are highly specific to the human PF4: heparin complex and are dependent on one or more of a relatively few amino acids at which the human sequence differs from rat. Human PF4 differs from rat at only six of the 52 C-terminal amino acid residues (37 proline, 38 threonine, 39 alanine, 49 arginine, 55 leucine, and 57 alanine).

We obtained the coordinates for the crystalline structure of human PF4 and have generated a model of PF4. It is of interest that 5 (amino acids 37,38,39,55, and 57) of the 6 C-terminal residues at which human and rat PF4 differ are located on the surface of the molecule where they could come in contact with heparin. Moreover, amino acid 39 (alanine in the human PF4, proline in the rat) and amino acid 55 (leucine in human, arginine in rat) are contiguous, being only 4.8 angstroms apart (in the absence of heparin).

Example 7

Linkage of Heparin Fragments to a Solid Surface to Provide a Site for PF4 Attachment and to Create Targets for HITP Antibody Binding Fragmentation of heparin (modified from J. Hoffman, et al., *Carbohydrate Research* 117: 328, 1983): Heparin (Sigma, 2.841 g, equal to 500,000 USP units, with a specific activity of 176 USP units/mg) was dissolved in 50 ml of distilled water, the pH was adjusted to 2.5 with 0.1 M of hydrochloric acid. A solution of sodium nitrite (15 mg) in 1 ml of water was added dropwise. The reaction mixture was stirred at room temperature for two hours. The pH was adjusted to neutrality with 0.1 M sodium hydroxide.

The mixture was dialyzed on a 3 kDa cutoff membrane (Spectrapor) against distilled water (three times, five one each time). The end product (180 ml) was divided in two aliquots of 90 ml each. One aliquot was filtered through a 0.2 micron filter and stored at 4° C. A second aliquot was freeze-dried for long-term storage. The loss of heparin during the procedure was estimated to be about 40%.

Coupling of Heparin Fragments to an Aminated Surface by Reductive Amination.

Alkylamine beads from Pierce (Rockford, Ill.) having a diameter of ¼" and approximately 3 μmoles of amino function per bead, were used in the procedure. The alkylamine residues on the beads have a 6 carbon spacer arm and a terminal amino group. Four ml of PBS (0.02 M pH 7.2) containing 36.9 mg of sodium cyano-borohydride ($NaBH_3CN$) were added to 25 ml (369.25 mg) of nitrous acid-treated heparin. Sodium cyanoborohydride was used to reduce the terminal aldehydic group of heparin, converting the labile Schiff base between the aldehyde and the amino group to a stable covalent linkage. The volume was brought to 50 ml by adding 21 more ml of PBS. Fourteen alkylamine beads were added, and the mixture was incubated on a rotator for 2 hours. The beads were washed three times using PBS with 0.05% Tween-20 and then blocked with 20% of FBS in PBS-TW for 30 minutes.

FIG. 6 shows the results of the reaction of an HITP antibody against immobilized heparin/PF4 complexes prepared by the method described above (open circles) compared to heparin cross-linked to the solid surface at multiple sites (the "cross-linking" method) prior to addition of PF4 (closed circles). Referring to FIG. 6, values on the abscissa are ODs obtained with an alkaline phosphatase-linked secondary probe recognizing bound IgG. Quantities of PF4 added to the immobilized heparin are shown in the ordinate.

FIG. 6 demonstrates that when using the method of the present invention to immobilize heparin, the amount of antibody bound increased with quantities of PF4 added. The same antibody bound poorly to heparin/PF4 complexes prepared according to the "cross-linking" method even when 10 or 20 μg of PF4 were added. Note also that intrinsic "background" OD (no PF4 added) was much less with the method of the present invention (about 0.05 OD) than with the "cross-linking" method (about 0.2 OD).

FIG. 7 describes a comparison between the method of the present invention and the method described in Amiral, et al. (supra) for detection of HITP antibodies. The dashed line in FIG. 7 indicates results obtained when the method of the present invention was used to prepare the target heparin/platelet factor 4 complexes. To couple nitrous acid digested heparin (NH) to biotin-LC-hydrazide (Pierce), 5.3 mg of biotin-LC-hydrazide, which includes a 13 residue spacer arm, together with 148 mg of NH and 15 mg of sodium cyano-borohydride ($NaBH_3CN$) was suspended in sodium acetate buffer (0.3 M, pH 5.2) to a final volume of 2 ml. The mixture was left on an orbital shaker for 4 hours, then dialyzed overnight against 5 liters of PBS (0.02 M, pH 7.2).

To link the NH-biotin-LC-hydrazide (NH-biotin) to a solid support, 1.25 μmoles of NH-biotin were then added to each well of a Reacti-Bind™ (Pierce) streptavidin coated polystyrene microtiter plate and incubated for 2 hours at room temperature. (The content of streptavidin per well is estimated to be about 6.6 μmoles.) Each well was rinsed three times with 300 μl of PBS Tw, blocked with 300 μl of PBS-Tw-FBS (20%) for 30 minutes, and washed. PF4 (0.025 μg/well) in 50 μl of PBS was added and incubated 1 hour at room temperature. Each well was again rinsed three times with 300 μl of PBS-Tw, blocked with 300 μl of PBS-Tw-FBS (20%) for 30 minutes and washed. Plasma samples (0.5 ml) diluted 1:10 were then added and bound antibody was detected as described.

Referring to FIG. 7, the solid lines indicate that heparin/platelet factor 4 complexes were created as described in Example 4, above.

Note that FIG. 7 demonstrates that the method of the present invention is not sensitive to heparin/platelet factor 4 ratios while the method described by Amiral, et al. only works over a limited ratio range.

We claim:

1. A method of detecting heparin-induced antibodies in a human patient, comprising:

(a) attaching a glycosaminoglycan to a solid support, wherein the glycosaminoglycan has a reducing terminal residue and is attached to the solid support only at the reducing terminal residue;

(b) binding human platelet factor 4 to the solid phase glycosaminoglycan, whereby a complex having an epitope which specifically binds to said heparin-induced antibodies is formed;

(c) contacting plasma or serum from said human patient to the complex;

(d) analyzing the complex to determine if antibodies have specifically bound thereto; and (e) detecting said heparin-induced antibodies by determining the antibodies specifically bound to the complex.

2. The method of claim 1 wherein step (d) comprises contacting the solid support of step c with a labelled anti-human antibody which specifically binds to any said heparin-induced antibodies bound to the complex and measuring the amount of the labelled anti-human antibody bound to the support.

3. The method of claim 2 wherein the labeled anti-human antibody is labeled with alkaline phosphatase and the measuring step further comprises contacting the bound labeled anti-human antibody with a substrate for the alkaline phosphates such that a measurable product is produced and correlated to the amount of heparin-induced antibodies present in the plasma or serum.

4. The method of claim 3 wherein the substrate is PNPP.

5. The method of claim 2 wherein the immunological component is anti-human IgG.

6. The method of claim 5 wherein the immunological component is selected from the group consisting of anti-human IgM and anti-human IgA.

7. The method of claim 1 wherein the solid support is an alkylamine-coated microtiter plate.

8. The method of claim 1 wherein the solid support is an alkylamine-coated bead.

9. The method of claim 1 wherein the glycosaminoglycan in step (a) is selected from the group consisting of heparin, heparin salts, metallic heparinates, heparamine, and heparan sulphate.

10. The method of claim 1 wherein the glycosaminoglycan is heparin.

11. The method of claim 10 wherein the platelet factor 4 is obtained by pooling platelets from normal whole blood and releasing platelet factor 4 by adding thrombin-receptor activating peptide (TRAP).

12. The method of claim 1 wherein the glycosaminoglycan is a heparin fragment having greater than 10 saccharide residues.

13. The method of claim 1 wherein the platelet factor 4 in step (b) is native platelet factor 4.

14. The method of claim 1 wherein step (c) includes incubating the plasma or serum with ecteola cellulose to remove residual heparin prior to testing the plasma or serum for the heparin-induced antibodies.

15. The method of claim 1 wherein step (c) includes diluting the plasma or serum in the amounts: 1 part plasma or serum to 10 parts or more of PBS (V/V) whereby background reactivity is reduced.

16. The method of claim 1 wherein the platelet factor in step (b) is selected from the group consisting of recombinant platelet factor 4 and synthetic platelet factor 4.

17. A kit for determining the presence or absence of heparin-induced antibodies, comprising in separate receptacles:

(a) a solid support prepared by first attaching a glycosaminoglycan to the solid support, wherein the glycosaminoglycan has a reducing terminal residue and is attached to the solid support only at the reducing terminal residue, and then adding human platelet factor 4, which binds spontaneously to the glycosaminoglycan to form a complex having an epitope specific to the heparin-induced antibodies;

(b) a labeled anti-human immunoglobulin antibody; and (c) a chromogenic substrate for the label.

18. The kit of claim 17 wherein the glycosaminoglycan of (a) is selected from the group consisting of heparin, heparin salts, metallic heparinates, heparamine, and heparan sulphate.

19. The kit of claim 18 wherein the glycosaminoglycan is heparin.

20. The kit of claim 17 wherein the platelet factor 4 of step (a) is native platelet factor 4.

21. The kit of claim 20 wherein the platelet factor 4 is recovered from normal human platelets using thrombin receptor activation peptide (TRAP) to activate the platelets and release the platelet factor 4.

22. The kit of claim 17 wherein the labeled anti-human immunoglobulin of step (b) comprises an enzyme label conjugated to a specific binding member selected from the group consisting of anti-human IgG, anti-human IgM, and anti-human IgA.

23. The kit of claim 22 wherein the enzyme is alkaline phosphatase.

24. The kit of claim 23 wherein the substrate is PNPP (p-nitrophenyl phosphate).

25. The kit of claim 17 wherein the platelet factor 4 of element (a) is selected from the group consisting of recombinant PF4 and synthetic PF4.

* * * * *

UNITED STATES PATENT AND TRADEMARK OFFICE
CERTIFICATE OF CORRECTION

PATENT NO. : 5,972,717
DATED : October 26, 1999
INVENTOR(S) : Richard H. Aster et al.

It is certified that error appears in the above-identified patent and that said Letters Patent is hereby corrected as shown below:

<u>Column 1,</u>
Line 2, after the title, please insert:
-- Statement Regarding Federally Sponsored Research or Development --
Line 3, please insert
--     This invention was made with United States government support awarded to the following agency: NIH HL 13629. The United States has certain rights in this invention. --

Signed and Sealed this

Thirtieth Day of September, 2003

JAMES E. ROGAN
*Director of the United States Patent and Trademark Office*

```
                    SEQUENCE LISTING (1) GENERAL INFORMATION:

(iii) NUMBER OF SEQUENCES: 3
```

(2) INFORMATION FOR SEQ ID NO:1:

(i) SEQUENCE CHARACTERISTICS:
        (A) LENGTH: 70 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:1:

```
Glu Ala Glu Glu Asp Gly Asp Leu Gln Cys Leu Cys Val Lys Thr Thr
1               5                   10                  15

Ser Gln Val Arg Pro Arg His Ile Thr Ser Leu Glu Val Ile Lys Ala
            20                  25                  30

Gly Pro His Cys Pro Thr Ala Gln Leu Ile Ala Thr Leu Lys Asn Gly
            35                  40                  45

Arg Lys Ile Cys Leu Asp Leu Gln Ala Pro Leu Tyr Lys Lys Ile Ile
        50                  55                  60

Lys Lys Leu Leu Glu Ser
65              70
```

(2) INFORMATION FOR SEQ ID NO:2:

(i) SEQUENCE CHARACTERISTICS:
        (A) LENGTH: 76 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:2:

```
Val Thr Arg Ala Ser Pro Glu Glu Ser Asp Gly Asp Leu Ser Cys Val
1               5                   10                  15

Cys Val Lys Thr Ser Ser Ser Arg Ile His Leu Lys Arg Ile Thr Ser
            20                  25                  30

Leu Glu Val Ile Lys Ala Gly Pro His Cys Ala Val Pro Glx Leu Ile
            35                  40                  45

Ala Thr Leu Lys Asn Gly Ser Lys Ile Cys Leu Asp Arg Gln Val Pro
        50                  55                  60

Leu Tyr Lys Lys Ile Ile Lys Lys Leu Leu Glu Ser
65              70                  75
```

(2) INFORMATION FOR SEQ ID NO:3:

(i) SEQUENCE CHARACTERISTICS:
        (A) LENGTH: 88 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:3:

```
Glu Ser Ser Phe Pro Ala Thr Phe Val Pro Leu Pro Ala Asp Ser Glu
1               5                   10                  15

Gly Gly Glu Asp Glu Asp Leu Gln Cys Val Cys Leu Lys Thr Thr Ser
            20                  25                  30

Gly Ile Asn Pro Arg His Ile Ser Ser Leu Glu Val Ile Gly Ala Gly
            35                  40                  45

Thr His Cys Pro Ser Pro Gln Leu Leu Ala Thr Lys Lys Thr Gly Arg
```

-continued

```
                50                  55                  60
Lys Ile Cys Leu Asp Gln Gln Arg Pro Leu Tyr Lys Lys Ile Leu Lys
 65                  70                  75                  80

Lys Leu Leu Asp Gly Asp Glu Ser
                 85
```